United States Patent [19]

Roth et al.

[11] Patent Number: 5,013,814
[45] Date of Patent: May 7, 1991

[54] ARALIPHATIC SULFONIUM SALTS AND THEIR USE

[75] Inventors: Martin Roth, Giffers; Beat Müller, Marly, both of Switzerland

[73] Assignee: Ciba-Geigy Corporation, Ardsley, N.Y.

[21] Appl. No.: 462,252

[22] Filed: Jan. 9, 1990

[30] Foreign Application Priority Data

Jan. 16, 1989 [CH] Switzerland ............ 129/89
Oct. 6, 1989 [CH] Switzerland ............ 3649/89

[51] Int. Cl.$^5$ .............. C08F 4/20; C08G 59/68; C08G 8/04; C08G 63/08
[52] U.S. Cl. .............. 528/90; 525/327.3; 528/139; 528/143; 528/356; 528/361; 528/365; 528/366; 528/393; 528/408; 528/409; 526/192; 526/222
[58] Field of Search .......... 528/90, 139, 143, 356, 528/361, 365, 366, 393, 408, 409; 525/327.3; 526/192, 222

[56] References Cited

U.S. PATENT DOCUMENTS

| | | | |
|---|---|---|---|
| 4,154,872 | 5/1979 | Tsao et al. | 528/90 X |
| 4,173,476 | 11/1979 | Smith | 528/90 X |
| 4,230,814 | 10/1980 | Crivello | 528/90 X |
| 4,336,363 | 6/1982 | Crivello | 528/90 X |
| 4,544,732 | 10/1985 | Corley | 528/90 |
| 4,554,342 | 11/1985 | Corley | 528/90 |
| 4,874,833 | 10/1989 | Kershaw | 528/90 X |

OTHER PUBLICATIONS

Chem. Abst. 28546b (1969).
J. Am. Chem. Soc., vol. 107, pp. 3224–3232 (1985).
Abstract for EP297,442.

Primary Examiner—Earl Nielsen
Attorney, Agent, or Firm—JoAnn Villamizar

[57] ABSTRACT

Sulfonium salts of the formulae I to IV

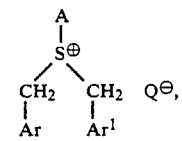

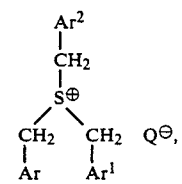

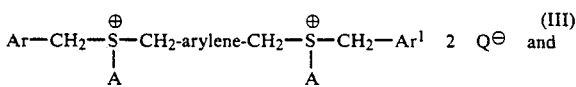

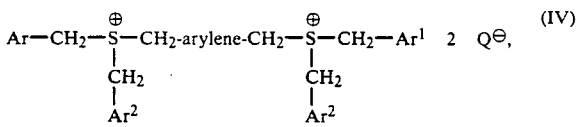

in which A is $C_1$–$C_{12}$ alkyl, $C_3$–$C_8$cycloalkyl, $C_4$–$C_{10}$cycloalkylalkyl, phenyl which is unsubstituted or mono- or polysubstituted by $C_1$–$C_8$alkyl, $C_1$–$C_4$alkoxy, halogen, nitro, phenyl, phenoxy, alkoxycarbonyl having 1–4 C atoms in the alkoxy radical or acyl having 1–12 C atoms, Ar, $Ar^1$ and $Ar^2$, independently of one another, are each unsubstituted or mono- or polysubstituted phenyl, or naphthyl which is unsubstituted or mono- or polysubstituted each arylene is an unsubstituted or mono- or polysubstituted phenylene or unsubstituted or mono- or polysubstituted naphthylene and $Q^\ominus$ is $SbF_6^-$, $AsF_6^-$ or $SbF_5OH^-$ are valuable curing agents and curing accelerators in the heat-curing of cationically polymerizable compounds, preferably epoxy resins.

8 Claims, No Drawings

ARALIPHATIC SULFONIUM SALTS AND THEIR USE

The present invention relates to novel araliphatic sulfonium salts, their use in curable mixtures containing cationically polymerizable compounds and to the products obtained from these mixtures by heat-curing.

It is known to use sulfonium salts as curing agents or curing accelerators in the heat-curing of cationically polymerizable organic compounds. The curing agents known from the Journal of Coatings Technology, Vol. 53, No. 675, Apr. 1981, pages 43-51, such as α-phenethyl-substituted sulfonium tetrafluoroborates, are slowly decomposed upon storage, so that the curable mixtures prepared using these sulfonium salts have only a relatively short pot life.

The epoxide formulations which are described in Journal of Applied Polymer Science, Vol. 32, 5727-5732 (1986) and contain monobenzylsulfonium salts are distinguished by a long pot life, although relatively long and thus uneconomical curing times are required to completely cure them.

It has now been found that certain araliphatic sulfonium salts when mixed with cationically polymerizable organic compounds have a distinct latency at room temperature, thus allowing a wide processing margin, and that rapid curing takes place upon heating the mixtures according to the invention to more than 100° C.

The invention relates to sulfonium salts of the formulae I to IV

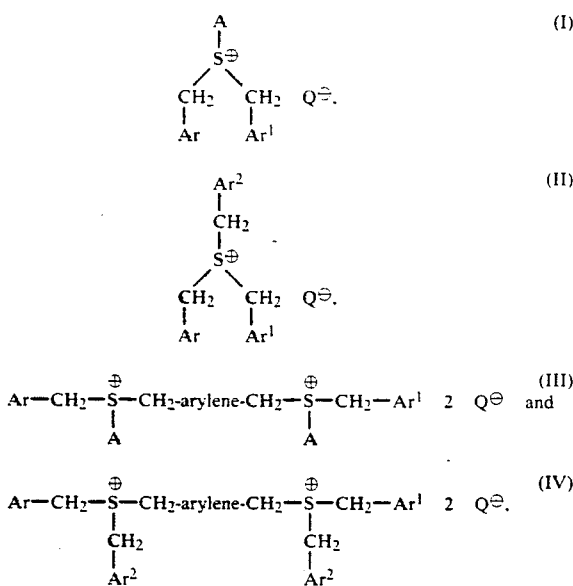

in which A is $C_1$-$C_{12}$alkyl, $C_3$-$C_8$cycloalkyl, $C_4$-$C_{10}$cycloalkylalkyl, phenyl which is unsubstituted or mono- or polysubstituted by $C_1$-$C_8$alkyl, $C_1$-$C_4$alkoxy, halogen, nitro, phenyl, phenoxy, alkoxycarbonyl having 1-4 C atoms in the alkoxy radical or acyl having 1-12 C atoms, Ar, $Ar^1$ and $Ar^2$, independently of one another, are each phenyl which is unsubstituted or mono- or polysubstituted by $C_1$-$C_8$alkyl, $C_1$-$C_4$alkoxy, halogen, nitro, phenyl, phenoxy, alkoxycarbonyl having 1-4 C atoms in the alkoxy radical or acyl having 1-12 C atoms or is naphthyl which is unsubstituted or mono-or polysubstituted by $C_1$-$C_8$alkyl, $C_1$-$C_4$alkoxy, halogen, nitro, phenyl, phenoxy, alkoxycarbonyl having 1-4 C atoms in the alkoxy radical or acyl having 1-12 C atoms, each arylene is phenylene which is unsubstituted or mono- or polysubstituted by $C_1$-$C_8$alkyl, $C_1$-$C_4$alkoxy, halogen, nitro, phenyl, phenoxy, alkoxycarbonyl having 1-4 C atoms in the alkoxy radical or acyl having 1-12 C atoms or naphthylene which is unsubstituted or mono-or polysubstituted by $C_1$-$C_8$alkyl, $C_1$-$C_4$alkoxy, halogen, nitro, phenyl, phenoxy, alkoxycarbonyl having 1-4 C atoms in the alkoxy radical or acyl having 1-12 C atoms and $Q^\ominus$ is $SbF_6^-$, $AsF_6^-$ or $SbF_5OH^-$.

Preferably, the invention relates to sulfonium salts of the formulae I and II

and $$\begin{array}{c} Ar^2 \\ | \\ CH_2 \\ | \\ S^\oplus \\ / \quad \backslash \\ CH_2 \quad CH_2 \quad Q^\ominus \\ | \quad\quad | \\ Ar \quad\quad Ar^1 \end{array} \quad (II)$$

in which A is $C_1$-$C_{12}$alkyl, $C_3$-$C_8$cycloalkyl, $C_4$-$C_{10}$cycloalkylalkyl, phenyl which is unsubstituted or mono- or polysubstituted by $C_1$-$C_8$alkyl, $C_1$-$C_4$alkoxy, halogen, nitro, phenyl, phenoxy, alkoxycarbonyl having 1-4 C atoms in the alkoxy radical or acyl having 1-12 C atoms, Ar, $Ar^1$ and $Ar^2$, independently of one another, are each phenyl which is unsubstituted or mono- or polysubstituted by $C_1$-$C_8$alkyl, $C_1$-$C_4$alkoxy, halogen, nitro, phenyl, phenoxy, alkoxycarbonyl having 1-4 C atoms in the alkoxy radical or acyl having 1-12 C atoms, or is naphthyl which is unsubstituted or mono-or polysubstituted by $C_1$-$C_8$alkyl, $C_1$-$C_4$alkoxy, halogen, nitro, phenyl, phenoxy, alkoxycarbonyl having 1-4 C atoms in the alkoxy radical or acyl having 1-12 C atoms, and $Q^\ominus$ is $SbF_6^-$, $AsF_6^-$ or $SbF_5OH^-$.

Preferably, A is $C_1$-$C_{12}$alkyl or phenyl which is unsubstituted or substituted by halogen or $C_1$-$C_4$alkyl, Ar, $Ar^1$ and $Ar^2$, independently of one another, are each phenyl which is unsubstituted or mono- or polysubstituted by $C_1$-$C_8$alkyl, $C_1$-$C_4$alkoxy, Cl or Br, and $Q^\ominus$ is $SbF_6^-$ or $SbF_5OH^-$, for example dibenzylethylsulfonium hexafluoroantimonate.

Particularly preferred sulfonium salts are those of the formula II in which Ar, $Ar^1$ and $Ar^2$, independently of one another, are each phenyl which is unsubstituted or substituted by $C_1$-$C_8$alkyl, $C_1$-$C_4$alkoxy, Cl or Br and $Q^\ominus$ is $SbF_6^-$ or $SbF_5OH^-$, such as in particular tribenzylsulfonium hexafluoroantimonate.

$C_1$-$C_{12}$alkyl as A in formula I can be straight-chain or branched. For example, A can be methyl, ethyl, isopropyl, n-butyl, sec-butyl, tert-butyl, n-octyl or n-dodecyl.

Examples of suitable cycloalkyls are cyclopropyl, cyclopentyl, cyclohexyl, and cyclooctyl.

Examples of suitable cycloalkylalkyls are cyclohexylmethyl and cyclohexylethyl.

A substituted phenyl or naphthyl as A, Ar, $Ar^1$ and $Ar^2$ can be identically or differently substituted phenyl or naphthyl. Examples are p-tolyl, xylyl, ethylphenyl, methoxyphenyl, ethoxyphenyl, p-chlorophenyl, 2,4-, 3,4- or 2,6-dichlorophenyl, bromophenyl, acetylphenyl, trimethylphenyl, methylnaphthyl, methoxynaphthyl, ethoxynaphthyl, chloronaphthyl, bromonaphthyl and biphenyl.

A substituted phenylene or naphthylene as arylene can be, for example, methylphenylene, ethylphenylene, methoxyphenylene, ethoxyphenylene, chlorophenylene, dichlorophenylene, bromophenylene, acetylphenylene, trimethylphenylene, methylnaphthylene, methoxynaphthylene, ethoxynaphthylene, chloronaphthylene or bromonaphthylene. Preferably, arylene is an unsubstituted phenylene or naphthylene.

The sulfonium salts according to the invention of the formulae I and II can be prepared by one of the processes disclosed in Houben-Weyl, Methoden der organischen Chemie (Methods of Organic Chemistry), Volume IX, pages 171 ff (1955), and supplement E 11, pages 405 ff (1985), by reacting, for example, a sulfide of the formula V $$Ar-CH_2-S-CH_2-Ar^1 \quad (V),$$

in which Ar and $Ar^1$ are as defined in formula I or II either (a) with molar amounts of an oxonium salt of the formula VI $$\begin{matrix} A \\ A-O^+ \;\; Z^-, \\ A \end{matrix} \quad (VI)$$

in which A is as defined in formula I and $Z^-$ is $Q^-$, $SbCl_6^-$, $BF_4^-$ or $PF_6^-$ to give compounds of the formula I or the formula Ia $$\begin{matrix} A \\ | \\ S^- \\ /\quad\backslash \\ CH_2 \quad CH_2 \;\; Za^- \\ | \quad\quad | \\ Ar \quad\;\; Ar^1 \end{matrix} \quad (Ia)$$

in which $Za^-$ is $SbCl_6^-$, $BF_4^-$ or $PF_6^-$ and subsequently reacting the compounds of the formula Ia by anion exchange with an alkali metal salt or a quaternary ammonium salt of the formula VII $$Y^-Q^- \quad (VII)$$

in which $Y^+$ is an alkali metal cation or $N(R_4)^+$ in which R is hydrogen or $C_1$-$C_4$alkyl and $Q^-$ is as defined in formula I to give a compound of the formula I, or (b) in the presence of a strong acid with at least a molar amount of an alcohol of the formula VIII $$Ar^2-CH_2-OH \quad (VIII),$$

in which $Ar^2$ is as defined in formula II, to give a sulfonium salt of this acid of the formula IIa $$\begin{matrix} Ar-CH_2 \\ \quad\quad\quad\backslash \\ Ar^1-CH_2-S^- \text{ (anion of the acid)}^- \\ \quad\quad\quad/ \\ Ar^2-CH_2 \end{matrix} \quad (IIa)$$

and subsequently reacting the sulfonium salt of the formula IIa with an alkali metal salt or a quaternary ammonium salt of the formula VII to give a compound of the formula II.

Analogously, the compounds according to the invention of the formulae III and IV can be prepared by reacting, for example, 1 mol of a compound of the formula IX $$Ar-CH_2-S-CH_2-arylene-CH_2-S-CH_2-Ar^1 \quad (IX)$$

in which Ar and $Ar^1$ are as defined in formula III or IV either (c) with 2 mol of an oxonium salt of the formula VI to give compounds of the formula III or the formula IIIa $$Ar-CH_2-\overset{\oplus}{\underset{A}{S}}-CH_2-arylene-CH_2-\overset{\oplus}{\underset{A}{S}}-CH_2-Ar^1 \;\; 2\;Za^{\ominus} \quad (IIIa)$$

in which $Za^-$ is $SbCl_6^-$, $BF_4^-$ or $PF_6^-$ and subsequently reacting the compound of the formula IIIa by anion exchange with an alkali metal salt or a quaternary ammonium salt of the formula VII to give a compound of the formula III, or (d) in the presence of a strong acid with 2 mol of an alcohol of the formula VIII to give a disulfonium salt of this acid of the formula IVa $$Ar-CH_2-\overset{\oplus}{\underset{Ar^2}{S}}-CH_2-arylene-CH_2-\overset{\oplus}{\underset{Ar^2}{S}}-CH_2-Ar^1 \;\; 2\;\text{(anion of the acid)}^{\ominus} \quad (IVa)$$

and subsequently reacting the disulfonium salt of the formula IVa with an alkali metal salt or a quaternary ammonium salt of the formula VII to give a compound of the formula IV.

The compounds of the formulae V, VI, VII, VIII and IX are known compounds, some of which are commercially available.

For example, sulfides of the formula V are described in Houben-Weyl, Volume 9, page 93 (1955), or Volume E 11, page 158 (1985) or are commercially available from Fluka and Aldrich Co.

Oxonium salts of the formula VI are known, for example, from Houben-Weyl, Volume 6/3, page 328 (1965), or from U.S. Pat. No. 3,585,227.

Alkali metal salts or quaternary ammonium salts of the formula VII, for example $NaSbF_6$, $NaAsF_6$ or $NH_4AsF_6$ are commercially available, for example from Morton Thiokol Co. Likewise, alcohols of the formula VIII, for example benzyl alcohol or chlorinated benzyl alcohols, are commercially available.

Compounds of the formula IX can be prepared in a known manner by reacting, for example, 1 mol of an unsubstituted or substituted $\alpha,\alpha'$-dihalogenomethylarylene of the formula X $$Hal-CH_2-arylene-CH_2-Hal \quad (X)$$

in the presence of alkali metal hydroxide solution with 2 mol of an unsubstituted or substituted mercaptan of the formula XI $$Ar-CH_2SH \text{ or } Ar^1-CH_2-SH \quad (XI)$$

to give compounds of the formula IX.

Compounds of the formula I or III in which A is the radical of the formula XII

 (XII)

in which R' and R", independently of one another, are each a hydrogen atom or together with the ethylene radical alkyl containing up to 12 C atoms or cycloalkyl containing up to 8 C atoms can also be prepared by reacting a sulfide of the formula V in the presence of a strong acid with at least a molar amount of an olefin of the formula XIII

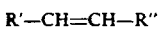 (XIII)

to give a sulfonium salt of the formula XIV or XV

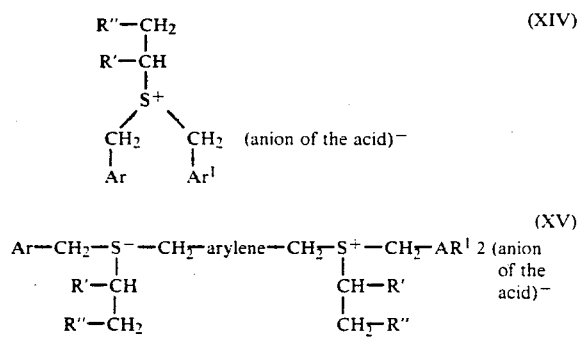

and subsequently reacting the sulfonium salt of the formula XIV or XV with an alkali metal salt or a quaternary ammonium salt of the formula VII to give a compound of the formula I or III in which A is the radical of the formula XII.

The olefins of the formula XIII used are, for example, ethylene, propylene, 1-butene, 2-butene, isobutylene, 1-pentene, 2-pentene, cyclobutene, cyclopentene or cyclohexene and the strong acids used are, for example, H$_2$SO$_4$, HPF$_6$, HBF$_4$, HClO$_4$ or CF$_3$SO$_3$H.

As mentioned at the beginning, the compounds according to the invention of the formulae I, II, III and IV are valuable curing agents and curing catalysts for the heat-curing of cationically polymerizable compounds.

The invention accordingly also relates to a curable mixture containing (a) at least one sulfonium salt of the formula I, II, III or IV and (b) at least one cationically polymerizable organic material.

Preferably, the mixtures according to the invention contain at least one sulfonium salt of the formula I or II.

Cationically polymerizable organic materials which are suitable for the curable mixtures according to the invention are, for example, of the types below, it being possible for these materials to be used by themselves or as mixtures of at least two components:

I. Ethylenically unsaturated compounds polymerizable by a cationic mechanism. These include
1. Monoolefins and diolefins, for example isobutylene, butadiene, isoprene, styrene, α-methylstyrene, divinylbenzenes, N-vinylpyrrolidone, N-vinylcarbazole and acrolein.
2. Vinyl ethers, for example methyl vinyl ether, isobutyl vinyl ether, trimethylolpropane trivinyl ether, ethylene glycol divinyl ether; cyclic vinyl ethers, for example 3,4-dihydro-2-formyl-(2H)-pyran (dimeric acrolein) and the 2-hydroxymethyl-3,4-dihydro-(2H)-pyran ester of 3,4-dihydro-(2H)-pyran-2-carboxylic acid.
3. Vinyl esters, for example vinyl acetate and vinyl stearate.

II. Cationically polymerizable heterocyclic compounds, for example ethylene oxide, propylene oxide, epichlorohydrin, glycidyl ethers of monohydric alcohols or phenols, for example n-butyl glycidyl ether, n-octyl glycidyl ether, phenyl glycidyl ether and cresyl glycidyl ether; glycidyl acrylate, glycidyl methacrylate, styrene oxide and cyclohexene oxide; oxetanes such as 3,3-dimethyloxetane and 3,3-di(chloromethyl)oxetane; tetrahydrofuran; dioxolanes, trioxane and 1,3,6-trioxacyclooctane; lactones such as β-propiolactone, γ-valerolactone and ε-caprolactone; thiiranes such as ethylene sulfide and propylene sulfide; epoxy resins; linear and branched polymers having glycidyl groups in the side chains, for example homopolymers and copolymers of polyacrylate and polymethacrylate glycidyl esters.

Of the abovementioned polymerizable compounds, of particular importance are the epoxy resins and in particular the diepoxides and polyepoxides and epoxy resin prepolymers of the type used for preparing crosslinked epoxy resins. The diepoxides and polyepoxides can be aliphatic, cycloaliphatic or aromatic compounds. Examples of these compounds are the glycidyl ethers and β-methyl glycidyl ethers of aliphatic and cycloaliphatic diols or polyols, for example those of ethylene glycol, 1,2-propanediol, 1,3-propanediol, 1,4-butanediol, diethylene glycol, polyethylene glycol, polypropylene glycol, glycerol, trimethylolpropane or 1,4-dimethylolcyclohexane or 2,2-bis(4-hydroxycyclohexyl)propane, the glycidyl ethers of diphenols and polyphenols, for example resorcinol, 4,4'-dihydroxydiphenylmethane, 2,2-(4,4'-dihydroxydiphenyl)propane novolaks and 1,1,2,2-tetrakis(4-hydroxyphenyl)ethane. Further examples are N-glycidyl compounds, for example the diglycidyl compounds of ethyleneurea, 1,3-propyleneurea or 5,5-dimethylhydantoin or 4,4'-methylenebis(5,5'-dimethylhydantoin), or those such as triglycidyl isocyanurate.

Further glycidyl compounds of industrial importance are the glycidyl esters of carboxylic acids, in particular di- and polycarboxylic acids. Examples of these are the glycidyl esters of succinic acid, adipic acid, azelaic acid, sebacic acid, phthalic acid, terephthalic acid, tetra- and hexahydrophthalic acid, isophthalic acid or trimellitic acid, or of dimerized fatty acids.

Examples of polyepoxides which are different from glycidyl compounds are the diepoxides of vinylcyclohexene and dicyclopentadiene, 3-(3',4'-epoxycyclohexyl)-8,9-epoxy-2,4-dioxaspiro[5.5]undecane, 3',4'-epoxycyclohexylmethyl 3,4-epoxycyclohexanecarboxylate, butadiene diepoxide or isoprene diepoxide, epoxidized linolic acid derivatives or epoxidized polybutadiene.

Preferred epoxy resins are diglycidyl ethers, which can be prelengthened, of dihydric phenols or dihydric aliphatic alcohols having 2 to 4 carbon atoms. Particular preference is given to the diglycidyl ethers, which can be prelengthened, of 2,2-bis(4-hydroxyphenyl)propane and bis(4-hydroxyphenyl)methane.

Other suitable cationically polymerizable compounds are phenolic resins.

Preferred phenolic resins are resols prepared from a phenol and an aldehyde. Suitable phenols include phenol itself, resorcinol, 2,2-bis(p-hydroxyphenyl)propane, p-chlorophenol, phenol substituted by one or two alkyl groups each having 1 to 9 carbon atoms, such as o-, m- and p-cresol, xylenols, p-tert-butylphenol and p-nonyl-phenol and also phenyl-substituted phenols, in particular p-phenylphenol. The aldehyde which is condensed with the phenol is preferably formaldehyde, but other aldehydes such as acid aldehyde and furfural are also suitable. If desired, a mixture of these curable phenol-/aldehyde resins can be used.

The preferred resols are condensation products of phenol, p-chlorophenol, resorcinol or o-, m- or p-cresol with formaldehyde.

The curable mixtures according to the invention can be obtained in any desired form, for example as homogeneous liquid mixtures or in homogeneous or non-homogeneous glassy form. Homogeneous glassy products can be obtained in a manner known per se, for example by liquefying solid polymerizable organic materials, if appropriate with the addition of suitable solvents, heating to temperatures above their glass transition temperature, addition of the curing agent according to formula I or II and cooling of the resulting mixture.

In the curable mixtures according to the invention, the amount of component (a) is in general 0.05 to 0.5% by weight, relative to the amount of (b).

If desired, further heat-curing agents (c), for example polycarboxylic acids, polycarboxylic anhydrides or polyphenols, can be present in the curable mixtures according to the invention, especially in the presence of an epoxy resin as cationically polymerizable compound. However, these curing agents must be free of functional groups which interfere in or inhibit the cationic curing by sulfonium salts, for example amino, nitrilo or phosphino groups. The relative amount of such a curing agent is less than the stoichimetric amount of the further curing agent necessary for the complete curing of (b).

In addition, the curable mixtures according to the invention can contain still further compounds copolymerizable with component (b), for example cyclic ethers or cyclic lactones, as reactive solvents. These reactive solvents are, for example, propylene carbonate, $\epsilon$-caprolactone, $\gamma$-butyrolactone or tetrahydrofurfuryl alcohol. These copolymerizable compounds must also be free of groups which interfere in or inhibit the cationic curing. In the case where copolymerizable compounds are used, their relative amount is in general between 1 and 50% by weight, relative to the amount of component (b), and the amount of component (a) is in general 0.05 to 5% by weight, relative to the amount of component (b) and the amount of the copolymerizable compound.

The curable mixtures according to the invention can also contain further known additives customarily used in the technology of polymerizable materials. Examples of these additives are pigments, dyes, fillers and reinforcing agents, glass fibres and other fibres, flame retardants, antistatics, flow-improving agents, antioxidants and light stabilizers.

The mixtures according to the invention have an unusually long pot life at room temperature, which is of particular advantage when they are processed in complicated applications.

Quite generally, the curable mixtures according to the invention can be used for the preparation of cured products and can be used in the formulation adapted to the particular specific field of application, for example in the form of coating materials, lacquers, moulding compounds, dip-coating resins, casting resins, impregnating resins, laminating resins, 1- or 2-component adhesives or matrix resins.

The mixtures according to the invention can be rapidly cured at relatively low temperatures. In general, temperatures in the range from 20° to 200° C., preferably from 60° to 180° C., in particular 80° to 150° C., are used for the curing. The mixtures according to the invention can also first be pre-cured at lower temperatures until the curable composition becomes a gel which is then followed by curing at elevated temperatures.

The products obtained from the mixtures according to the invention by heat-curing are distinguished in particular by a high $T_G$ value and high temperature resistance. Furthermore, the invention accordingly also relates to the product obtained by heat-curing of the mixtures according to the invention, which are solid, insoluble and unmeltable products which are crosslinked in three dimensions.

The curing is usually carried out in combination with moulding to give moulded, impregnated, coated or bonded products.

EXAMPLE 1

A mixture of 1.07 g (5 mmol) of dibenzyl sulfide and 1.70 g (5 mmol) of triethyloxonium hexafluoroantimonate in 20 ml of methylene chloride is stirred under nitrogen at room temperature (RT) for 2½ hours (h). The colourless solution is extracted with water, and the organic phase is dried over magnesium sulfate. The solvent is removed on a rotary evaporator, the crystalline residue is washed with a small amount of toluene and dried in vacuo at room temperature.

This gives 2.20 g (92% of theory) of dibenzylethylsulfonium hexafluoroantimonate in the form of colourless crystals of melting point 119°–121° C.

Elemental analysis for $C_{16}H_{19}SSbF_6$: Calculated: (%) C=40.11 H=4.00 S=6.69; Found: (%) C=39.91 H=4.03 S=6.88.

$^1$H-NMR (100 MHz, $d_6$-acetone) in ppm: 1.41 (triplet, 3H); 3.50 (quartet, 2H); 4.91 (singlet, 4H); 7.53 (multiplet, 10H).

EXAMPLE 2

(a) 21.4 g (0.1 mol) of dibenzyl sulfide and 10.8 g (0.1 mol) of benzyl alcohol in 300 ml of acetic acid are initially introduced into a 750 ml reaction vessel equipped with stirrer, thermometer and dropping funnel.

20 ml of concentrated sulfuric acid are added dropwise with stirring over a period of 5 minutes (min). The reaction mixture is then heated in an oil bath to an inside temperature of 70° C. and stirred for 2 hours. The major portion of the acetic acid is distilled off, and the residue is poured into 200 ml of water. The suspension is left at 0°–5° for ½ hour, the crystalline residue is filtered off and dried in vacuo at RT. 36.5 g (91% of theory) of tribenzylsulfonium hydrogen sulfate remain in the form of colourless crystals of melting point 170° C. (decomposition).

(b) 16.64 g (0.041 mol) of tribenzylsulfonium hydrogen sulfate are dissolved in 750 ml of warm methanol. 16.04 g (0.062 mol) of solid sodium hexafluoroantimonate are added to the cloudy solution, which is stirred at RT for 1 hour. After adding a spatula of activated carbon, the mixture is filtered, and 750 ml of water are added to the clear filtrate. The precipitated crystals are filtered off, dried, washed with 100 ml of ether and dried again. This gives 16.41 g (74% of theory) of tribenzylsulfonium hexafluoroantimonate in the form of colourless crystals of melting point 170° C. (decomposition).

Elemental analysis for $C_{21}H_{21}SSbF_6$: Calculated: (%) C=46.61 H=3.91 S=5.92; Found: (%) C=47.44 H=3.99 S=6.09.

$^1$H-NMR (100 MHz, $d_6$-DMSO) in ppm: 4.78 (singlet, 6 H); 7.32 (singlet-like peak, 15 H).

EXAMPLE 3

(a) 10.7 g (0.050 mol) of dibenzyl sulfide and 5.4 g (0.050 mol) of benzyl alcohol in 50 ml of acetic acid are initially introduced into a 350 ml reaction vessel equipped with stirrer, thermometer and dropping funnel, and the mixture is heated to 50° C. in an oil bath.

A solution of 35.4 g (0.186 mol) of p-toluenesulfonic acid monohydrate in 100 ml of acetic acid is then added dropwise with stirring. Stirring at an inside temperature of 80° C. is then continued for 4 hours. The major portion of acetic acid is removed by distillation in a rotatory evaporator, and 100 ml of water and 50 ml of methylene chloride are added to the residue. The mixture is shaken, the methylene chloride phase is separated off, dried over magnesium sulfate and concentrated in a rotary evaporator. 23.6 g (99% of crude yield) of a yellowish oil remain. This oil is stirred in 130 ml of toluene, resulting in crystallization. After filtration and drying, 11.1 g (47% of theory) of tribenzylsulfonium p-toluenesulfonate remain in the form of colourless crystals.

Elemental analysis for $C_{28}H_{28}S_2O_3$: Calculated: (%) C=70.56 H=5.92 S=13.45; Found: (%) C=69.79 H=6.01 S=13.60.

$^1$H-NMR (100 MHz, $d_6$-DMSO) in ppm: 2.34 (singlet, 3 H); 4.85 (singlet, 6 H); 7.30/7.70 (multiplet, 19 H).

(b) 9.53 g (0.020 mol) of tribenzylsulfonium p-toluenesulfonate are dissolved in a mixture of 60 ml of methanol and 40 ml of water by slight warming. At RT, 6.84 g (0.030 mol) of solid potassium hexafluoroarsenate are added, and the suspension is stirred for 2 hours. The crystalline solid is filtered off and dried in vacuo at RT. This gives 9.48 g (96% of theory) of tribenzylsulfonium hexafluoroarsenate in the form of colourless crystals.

Elemental analysis for $C_{21}H_{21}SAsF_6$: Calculated: (%) C=51.02 H=4.28 S=6.49; Found: (%) C=50.94 H=4.34 S=6.48.

$^1$H-NMR (100 MHz, $d_6$-DMSO), in ppm: 4.69 (singlet, 6 H); 7.33 (multiplet, 15H).

EXAMPLE 4

(a) A solution of 108.06 g (0.45 mol) of sodium sulfite monohydrate and 6.0 g of tetrabutylammonium hydrogen sulfate (phase transfer catalyst) in 120 ml of water is added to a reaction vessel equipped with stirrer, thermometer and heated dropping funnel. 96.6 g (0.60 mol) of 4-chlorobenzyl chloride which has been melted at 50° C. and maintained at this temperature are added dropwise over a period of 50 minutes with vigorous stirring, while maintaining the inside temperature at 40°-50° C. Stirring at RT is continued for another 3 hours, the mixture is extracted with 200 ml of diethyl ether, the ether phase is washed 3 times with aqueous sodium chloride solution (half-saturated), dried over magnesium sulfate, filtered, and the ether is removed in a rotary evaporator. The residue is suspended in 100 ml of methanol, the mixture is filtered, and the filter residue is dried. This gives 79.7 g (94% of theory) of solid colourless di(4-chlorobenzyl) sulfide of melting point 42°-44° C.

Elemental analysis for $C_{14}H_{12}Cl_2S$: Calculated: (%) C=59.37 H=4.27 S=11.32 Cl=25.04; Found: (%) C=59.13 H=4.35 S=11.44 Cl=25.14.

$^1$H-NMR (100 MHz, CDCl$_3$) in ppm: 3.54 (singlet, 4 H); 7.2 (multiplet, 8 H).

(b) 28.6 g of a solution of HBF$_4$ in ether (HBF$_4$ content=54% by weight) are added dropwise to a solution of 22.7 g (0.080 mol) of di-(4-chlorobenzyl)sulfide and 13.7 g (0.096 mol) of chlorobenzyl alcohol in 64 ml of methylene chloride with stirring at such a rate that the inside temperature remains between 15° and 25° C. Stirring at room temperature is continued for another 2 hours, the mixture is diluted with methylene chloride, and the organic phase is washed 3 times with half-saturated sodium chloride solution. It is dried over magnesium sulfate, filtered, and the solvent is distilled off on a rotary evaporator. The solid residue is suspended in 80 ml of toluene, and the suspension is filtered. The residue is dried, after which 33.6 g (85% of theory) of tris(4-chlorobenzyl)sulfonium tetrafluoroborate remain in the form of colourless crystals of melting point 154°-156° C.

Elemental analysis for $C_{21}H_{18}Cl_3S.BF_4$: Calculated: (%) C=50.89 H=3.66 S=6.47 Cl=21.46; Found: (%) C=50.98 H=3.80 S=6.56 Cl=21.55

$^1$H-NMR (100 MHz, $d_6$-DMSO) in ppm: 4.76 (singlet, 6 H); 7.4 (singlet, 12 H).

(c) 66.95 g (0.135 mol) of tris(4-chlorobenzyl)sulfonium tetrafluoroborate are dissolved in a 500 ml round-bottomed flask in 300 ml of methylene chloride under N$_2$, and the mixture is cooled to 0° to 5° C. 26.0 g (0.24 mol) of sodium hexafluoroantimonate are then added, stirring at the same temperature is continued for 4 hours, and the suspension is then filtered.

The filtrate is freed from solvent on a rotary evaporator, and the residue is stirred in 300 ml of water at RT for 2¼ hours, the residue is filtered off and washed twice with water. The crude product is dried at RT overnight in a high vacuum. This gives 91.8 g (115.3% of theory) as the crude product.

The crude product is dissolved in 285 ml of isopropanol at 90° C., and the solution is cooled to 0°-5° C. The precipitated crystals are filtered and washed with a small amount of cooled isopropanol (0°-5° C.). The residue is dried at RT overnight on a high-vacuum pump. This gives 74.4 g (93.5% of theory) of dry tris(4-chlorobenzyl)sulfonium hexafluoroantimonate of melting point 132°-134° C.

Elemental analysis for $C_{21}H_{18}Cl_3SSbF_6$: Calculated: (%) C=39.13 H=2.81 S=4.97 Cl=16.5 F=17.68 Sb=18.99; Found: (%) C=39.1 H=2.9 S=4.9 Cl=16.5 F=17.4 Sb=19.6.

$^1$H-NMR (100 MHz in CDCl$_3$) in ppm: 7.1 (quartet: 12 H); 4.5 (singlet: 6 H).

EXAMPLE 5

(a) A solution of 269.0 g (1.12 mol) of sodium sulfide hydrate and 12.0 g of tetrabutylammonium hydrogen sulfate (phase transfer catalyst) in 300 ml of water is placed in a reaction vessel equipped with a stirrer and thermometer. 212.6 g (1.52 mol) of 4-methylbenzyl chloride are added dropwise below 40° C. over a period of 30 minutes with vigorous stirring. The reaction mixture is stirred at RT for 4½ hours and then at 50°-60° C. for ½ hour. The reaction mixture is cooled to 0°-5° C. and maintained at this temperature for ½ hour. The reaction mixture is filtered, and the residue is dissolved in about 2 litres of ethyl acetate. The organic phase is extracted twice with deionized water (pH ~ 6) and dried over MgSO$_4$. The ethyl acetate is removed on a rotary evaporator. The residue is dried at RT overnight in a high vacuum. This gives 174.8 g (95% of theory) of di(p-methylbenzyl) sulfide in the form of slightly yellowish white crystals of melting point 74°-76° C.

Elemental analysis for C$_{16}$H$_{18}$S: Calculated: (%) C=79.29 H=7.49 S=13.23; Found: (%) C=79.16 H=7.3 S=13.47.

$^1$H-NMR (100 MHz, CDCl$_3$) in ppm: 2.33 (singlet, 6 H); 3.56 (singlet, 4 H); 7.15 (singlet, 8 H).

(b) 85.1 g (0.351 mol) of di(p-methylbenzyl) sulfide and 51.5 g (0.421 mol) of p-methylbenzyl alcohol in 250 ml of methylene chloride are initially introduced into a reaction vessel (750 ml) equipped with stirrer and thermometer under an N$_2$ atmosphere. 142.7 g of an approximately 54% by weight HBF$_4$ solution in diethyl ether are added dropwise at an inside temperature of 20°-30° C. over a period of 40 minutes with stirring. The reaction mixture is stirred at RT for 2 hours. The reaction mixture is diluted with methylene chloride and extracted 4 times with deionized water (pH 5-6). The organic phase is dried with MgSO$_4$, and the methylene chloride is removed on a rotary evaporator. The product which is not completely freed of methylene chloride is stirred in 250 ml of toluene at RT for about 1 hour and then at 0°-5° C. for 1 hour. The precipitated crystals are filtered off with suction and washed with a small amount of toluene. The product is dried at room temperature for 19 hours in a high vacuum. This gives 118.6 g of tris(p-methylbenzyl)sulfonium tetrafluoroborate in the form of white crystals of melting point 168°-170° C.

$^1$H-NMR (100 MHz, d$_6$-acetone) in ppm: 2.33 (singlet, 9 H); 4.83 (singlet, 6 H); 7.25 (quartet, 12 H).

(c) Analogously to Example 4c), 100 g (230 mmol) of tris(p-methylbenzyl)sulfonium tetrafluoroborate are reacted with 119.0 g (460 mmol) of sodium hexafluoroantimonate. Recrystallization in isopropanol gives 117.1 g (87% of theory) of tris(p-methylbenzyl)sulfonium hexafluoroantimonate in the form of white crystals of melting point 88°-91° C.

Elemental analysis Calculated: (%) C=49.42 H=4.67 S=5.5; Found: (%) C=49.8 H=4.6 S=6.4.

$^1$H-NMR (100 MHz, d$_6$-acetone) in ppm: 2.34 (singlet, 9 H); 4.85 (singlet, 6 H); 7.25 (quartet, 12 H).

EXAMPLE 6

(a) A solution of 75.0 g (0.374 mol) of benzyl phenyl sulfide, 60.73 g (0.561 mol) of benzyl alcohol and 350 ml of methylene chloride are placed in a reaction vessel equipped with stirrer and thermometer. 182.45 g (1.12 mol) of 54% by weight of HBF$_4$ in diethyl ether are added dropwise at an inside temperature of 20°-30° C. over a period of 35 minutes with stirring. The reaction mixture is then stirred at RT for 2 hours. The reaction mixture is diluted with 300-400 ml of methylene chloride and extracted 4 times with water (pH ~ 6). The organic phase is then dried over MgSO$_4$, and the solvent is removed on a rotary evaporator. The remaining yellow-brown oil is stirred in 400 ml of toluene, and the product is allowed to crystallize at 0°-5° C. for about 1 hour. The suspension is filtered, and the residue is washed with a small amount of cooled toluene (0°-5° C.). The pure product is dried at RT overnight in a high vacuum. This gives 123.8 g (87% of theory) of dibenzylphenylsulfonium tetrafluoroborate in the form of white crystals of melting point 110°-115° C.

$^1$H-NMR (in d$_6$-acetone, 100 MHz) in ppm: 5.30 (quartet, 4 H); 7.22-8.02 (multiplet, 15 H).

(b) A mixture of 123.0 g (0.325 mol) of dibenzylphenylsulfonium tetrafluoroborate in 400 ml of methylene chloride is dissolved in a 2 liter round-bottomed flask at RT under N$_2$ until a clear solution is obtained. 117.8 g of sodium hexafluoroantimonate are then added, and the mixture is stirred at RT for 3½ hours. The suspension is then filtered through silica gel, and the solvent is removed from the filtrate on a rotary evaporator. The slightly reddish viscous residue is again dissolved in 250 ml of methanol and, after the addition of 250 ml of water, the product is allowed to crystallize at RT for 1-2 hours. The suspension is filtered, and the residue is washed with water. The product is then dried at RT overnight in a high vacuum. This gives 163.9 g (95% of theory) of dibenzylphenylsulfonium hexafluoroantimonate in the form of white crystals of melting point 105°-109° C.

Elemental analysis Calculated: (%) C=45.6 H=3.63 S=6.08 Sb=23.09 F=21.62; Found: (%) C=46.5 H=3.7 S=6.1 Sb=22.4 F=20.6.

$^1$H-NMR (d$_6$-acetone; 100 MHz) in ppm: 5.37 (quartet, 4 H); 7.25-8.04 (multiplet, 15 H).

EXAMPLE 7

(a) 5.66 g (20 mmol) of di(4-chlorobenzyl) sulfide, prepared according to Example 4(a), are reacted with 2.6 g (24 mmol) of benzyl alcohol and 8.13 g (50 mmol) of 54% by weight HBF$_4$ in 20 ml of methylene chloride as described in Example 6(a). This gives 7.44 g (80% of theory) of di(4-chlorobenzyl)phenylsulfonium tetrafluoroborate in the form of white crystals of melting point 123°-125° C.

$^1$H-NMR (100 MHz, CDCl$_3$) in ppm: 4.71 (singlet, 6 H); 7.27 (doublet, 12 H).

(b) A mixture of 7.0 g (15.2 mmol) of di(4-chlorobenzyl)phenylsulfonium tetrafluoroborate and 25 ml of methylene chloride is stirred in a 100 ml round-bottomed flask under N$_2$ until a clear solution is formed, which is then cooled to 0°-5° C. At this temperature, 5.9 g (22.8 mmol) of sodium hexafluoroantimonate are added, and the mixture is stirred for about 3 hours. The reaction mixture is filtered, and the filtrate is freed from the solvent on a rotary evaporator. 50 ml of deionized water are then added to the residue, and the product is allowed to crystallize at 0°-5° C. for 1-2 hours. The crystals which are obtained by filtration are washed with water and dried at RT overnight in a high vacuum. This gives 8.26 g of di(4-chlorobenzyl)phenylsulfonium hexafluoroantimonate in the form of white crystals of melting point 75°-77° C.

Elemental analysis Calculated: (%) C=41.34 H=3.14 S=5.26 Cl=11.62; Found: (%) C=41.24 H=3.15 S=5.08 Cl=12.37.

$^1$H-NMR (100 MHz) in ppm: 5.0 (multiplet, 6 H); 7.44 (multiplet, 13 H).

EXAMPLE 8

(a) 51.4 g (0.263 mol) of 2,4-dichlorobenzyl chloride, 47.4 g (0.197 mol) of sodium sulfide hydrate and 2.5 g of tetrabutylammonium hydrogen sulfate in 60 ml of water are reacted as in Example 5a). This gives 45.9 g (99% of theory) of bis(2,4-dichlorobenzyl) sulfide in the form of a yellowish clear liquid.

Elemental analysis Calculated: (%) C=47.76 H=2.86 S=9.11 Cl=40.28; Found: (%) C=47.4 H=2.9 S=8.3 Cl=41.64.

$^1$H-NMR (100 MHz, CDCl$_3$) in ppm: 3.74 (singlet, 4 H); 7.12–7.41 (multiplet, 6 H).

(b) 7.04 g (20 mmol) of bis(2,4-dichlorobenzyl) sulfide, 4.75 g (26.8 mmol) of 2,4-dichlorobenzyl alcohol and 9.26 g (57 mmol) of 54% by weight HBF$_4$ (in diethyl ether) in 16 ml of methylene chloride are reacted as in Example 5(b). This gives 3.76 g (31% of theory) of tris(2,4-dichlorobenzyl)sulfonium tetrafluoroborate in the form of white crystals of melting point 180°–182° C.

$^1$H-NMR (100 MHz, d$_6$-acetone) in ppm: 5.22 (singlet, 6 H); 7.2–7.85 (multiplet, 9 H).

(c) 3.5 g (5.8 mmol) of the product obtained according 5(b) are reacted with 2.99 g (11.6 mmol) of sodium hexafluoroantimonate in 35 ml of methylene chloride as in Example 7(c) to give 3.99 g (91.9% of theory) of a crude product. The crude product is suspended in 10 ml of isopropanol, and the mixture is stirred at RT for 1 hour. The suspension is then cooled to 0°–5° C., filtered, and the residue is dried at RT overnight in a high vacuum. This gives 3.45 g (79.5% of theory) of tris(2,4-dichlorobenzyl)sulfonium tetrafluoroantimonate in the form of white crystals of melting point 158°–160° C.

Elemental analysis Calculated: (%) C=33.7 H=2.02 S=4.29 Cl=28.44 F=15.24 Sb=16.28; Found: (%) C=33.4 H=2.1 S=4.1 Cl=28.7 F=14.7 Sb=16.5.

$^1$H-NMR (100 MHz, d$_6$-acetone) in ppm: 5.3 (singlet, 6 H); 7.4–7.8 (multiplet, 9 H)

EXAMPLE 9

(a) A mixture of 129.7 g (0.54 mol) of sodium sulfide hydrate, 8.74 g of tetrabutylammonium hydrogen sulfate and 145 ml of water are stirred at room temperature in a reaction vessel equipped with stirrer and thermometer, until a solution is obtained. 141.67 g (0.72 mol) of 3,4-dichlorobenzyl chloride are added over a period of 10 minutes with vigorous stirring at such a rate that the inside temperature does not exceed 50° C. The reaction mixture is then stirred at RT for 3½ hours. The reaction mixture is filtered, and the residue is dried in a high vacuum pump. The crude product is dissolved in 160 ml of refluxing ethyl acetate and then allowed to crystallize at 0°–5° C. for 1–2 hours. The recrystallized product is filtered off and dried at RT overnight in a high vacuum. This gives 98.37 g (77.6% of theory) of bis(3,4-dichlorobenzyl) sulfide in the form of white crystals of melting point 98°–99° C.

$^1$H-NMR (100 MHz, CDCl$_3$) in ppm: 3.53 (singlet, 4 H); 7.03–7.42 (multiplet, 6 H).

(b) 14.08 g (40 mmol) of bis(3,4-dichlorobenzyl) sulfide and 10.47 g (58.8 mmol) of 3,4-dichlorobenzyl alcohol in 50 ml of methylene chloride are initially introduced under an N$_2$ atmosphere into a reaction vessel equipped with stirrer and thermometer. 20.15 g (123.9 mmol) of hydrogen tetrafluoroborate (54% in diethyl ether) are added dropwise to the solution over a period of 10 minutes at an inside temperature of 20°–30° C. with stirring, and the reaction mixture is stirred at RT for 4 hours. Another 1.13 g of hydrogen tetrafluoroborate (54% in diethyl ether) are added to the reaction mixture and stirring at RT is continued for 3 hours. The reaction mixture is then filtered, and the residue is dried at RT in a high vacuum. The crude product is again stirred in 100 ml of water at RT, filtered, and the residue is dried at RT overnight in a high vacuum. This gives 18.3 g (76.41% of theory) of tris(3,4-dichlorobenzyl) sulfonium tetrafluoroborate in the form of white crystals of melting point 201°–203° C.

$^1$H-NMR (100 MHz, DMSO) in ppm: 4.8 (singlet, 6 H); 7.32–7.64 (multiplet, 9 H).

(c) A mixture of 7.5 g (12.71 mmol) of tris(3,4-dichlorobenzyl)sulfonium tetrafluoroborate and 220 ml of acetone are stirred in a 3-necked flask at about 30° C. under nitrogen, until a solution is obtained, and 4.93 g (19.06 mmol) of sodium hexafluoroantimonate are added. The reaction mixture is stirred at RT for 3 hours, 220 ml of methylene chloride are then added, and the mixture is stirred at RT for 1 hour. The suspension is filtered through kieselguhr, and the filtrate is freed from the solvents on a rotary evaporator. The residue is again stirred at RT in 50 ml of water, the mixture is filtered, and the solid product is dried at RT in a high vacuum. This gives 9.46 g (99.47% of theory) of white crystals (crude product 1).

9.46 g of crude product 1 are dissolved at RT in 75 ml of acetone. Under nitrogen, 4.2 g (16 mmol) of sodium hexafluoroantimonate are added, and the mixture is stirred at room temperature for ¾ hour. 100 ml of methylene chloride are added, the reaction mixture is filtered after 25 minutes through kieselguhr, and the filtrate is freed from the solvents on a rotary evaporator. The residue is stirred at RT in 50 ml of water, the mixture is filtered, and the residue is dried at RT overnight in a high vacuum. This gives 8.42 g of white crystals (crude product 2).

Crude product 2 is dissolved in 110 ml of methanol at 50°–60° C., and 150 ml of water are added. The suspension is stirred at RT for 3 hours, cooled to 0°–5° C., filtered, and the residue is washed with a small amount of water. The purified product is dried at RT overnight in a high vacuum. This gives 7.74 g (81% of theory) of tris(3,4-dichlorobenzyl)sulfonium hexafluoroantimonate in the form of white crystals of melting point 164°–166° C.

$^1$H-NMR (100 MHz, d$_6$-acetone) in ppm: 5.17 (singlet, 6 H); 7.44–7.67 (multiplet, 9 H).

EXAMPLE 10

(a) A mixture of 98.8 g (0.411 mol) of sodium sulfide, 5.0 g of tetrabutylammonium hydrogen sulfate and 110 ml of water are stirred in a reaction vessel equipped with a stirrer, thermometer and heatable dropping funnel, until a solution is obtained. 107.2 g of melted 2,6-dichlorobenzyl chloride are added with vigorous stirring over a period of 25 minutes at such a rate that the inside temperature does not exceed 55° C. The reaction mixture is worked up as in Example 9(a) to give 77.6 g (80% of theory) of bis(2,6-dichlorobenzyl) sulfide in the form of white crystals of melting point 128°–130° C.

Elemental analysis Calculated: (%) C=47.76 H=2.86 Cl=40.28 S=9.11; Found: (%) C=47.7 H=2.95 Cl=40.1 S=8.96.

$^1$H-NMR (100 MHz, CDCl$_3$) in ppm: 4.18 (singlet, 4 H); 7.02–7.35 (multiplet, 6 H).

(b) In a reaction vessel equipped with stirrer and thermometer, 14.1 g (40 mmol) of bis(2,6-dichlorobenzyl) sulfide and 9.5 g (53.6 mmol) of 2,6-dichlorobenzyl alcohol are dissolved under a N$_2$ atmosphere in 72 ml of methylene chloride. 18.53 g (114 mmol) of hydrogen tetrafluoroborate (54% in diethyl ether) are added dropwise at an inside temperature of 20°–30° C. over a period of 20 minutes with stirring, and the reaction mixture is stirred for 4 hours. Afterwards, another 2.26 g (13.9 mmol) of HBF$_4$ are added to the reaction mixture at RT, and stirring is continued for 1 hour. The reaction mixture is filtered, and the solvent is removed on a rotary evaporator. The residue is stirred in 100 ml of water at RT, the mixture is filtered, and the residue is dried at RT overnight in a high vacuum. This gives 17.49 g (74.25% of theory) of tris(2,6-dichlorobenzyl)-sulfonium tetrafluoroborate in the form of white crystals of decomposition point 185°–195° C.

(c) A mixture of 15.0 g (25 mmol) of tris(2,6-dichlorobenzyl)sulfonium tetrafluoroborate in 250 ml of methylene chloride is stirred in a 3-necked flask at about 30° C., until a solution is obtained, and then reacted with sodium hexafluoroantimonate at RT as in Example 9(c). Workup of the reaction mixture according to Example 9c) gives 12.6 g (67.4% of theory) of tris(2,6-dichlorobenzyl)sulfonium hexafluoroantimonate in the form of white crystals of melting point 216°–218° C.

$^1$H-NMR (100 MHz, CDCl$_3$) in ppm: 5.61 (singlet, 6 H); 7.67 (singlet, 9 H).

EXAMPLE 11

In a reaction vessel equipped with stirrer and thermometer, 15.64 g (0.108 mol) of 4-chlorothiophenol, 16.10 g (0.100 mol) of 4-chlorobenzyl chloride, 100 ml of toluene and 0.3 g of tetrabutylammonium hydrogen sulfate are stirred at RT, until a solution is obtained. 20.0 g (0.15 mol) of 30% aqueous sodium hydroxide solution are then added in portions with thorough stirring, and the reaction mixture is stirred at RT for 3 hours. It is diluted with a small amount of water, and the organic phase is extracted 3 times with neutral water, and the organic phase is dried over MgSO$_4$. The solvent is removed on the rotary evaporator, the residue is stirred in 30 ml of methanol/water (9:1), the mixture is filtered, and the purified product is dried at RT for 4 hours in a high vacuum. This gives 24.1 g (89% of theory) of 4-chlorophenyl 4-chlorobenzyl sulfide in the form of colourless crystals of melting point 67°–69° C.

Elemental analysis Calculated: (%) C=58.0 H=3.74 S=11.91 Cl=26.34; Found: (%) C=57.83 H=3.8 S=12.13 Cl=26.21.

$^1$H-NMR (100 MHz, CDCl$_3$) in ppm: 4.02 (singlet, 2 H); 7.20 (singlet, 8 H).

(b) 5.2 g (19.4 mmol) of 4-chlorophenyl 4-chlorobenzyl sulfide, 4.14 g (29.0 mmol) of 4-chlorobenzyl alcohol and 14.15 g (87 mmol) of hydrogen tetrafluoroborate (54% in diethyl ether) in 20 ml of methylene chloride are reacted as in Example 6(a) to give 7.23 g (77.4% of theory) of 4-chlorophenylbis(4-chlorobenzyl)sulfonium tetrafluoroborate in the form of white-beige crystals of melting point 147°–148° C.

$^1$H-NMR (100 MHz, d$_6$-acetone) in ppm: 5.4 (quartet, 4 H); 7.34–8.12 (multiplet, 12 H).

(c) In a 3-necked flask, 6.88 g (14.3 mmol) of 4-chlorophenylbis(4-chlorobenzyl)sulfonium tetrafluoroborate are dissolved under nitrogen at RT in 50 ml of methylene chloride. 5.54 g (21.4 mmol) of sodium hexafluoroantimonate are added, and the reaction mixture is stirred at RT for 3½ hours. The suspension is filtered, and the solvent is removed from the filtrate on a rotary evaporator. The residue is stirred in 50 ml of methanol, and 100 ml of water are added. The suspension is stirred at RT for ½ hour and at 0°–5° C. for ½ hour, then filtered, and the residue is dried at RT overnight in a high vacuum. This gives 8.0 g (88.7% of theory) of 4-chlorophenylbis(4-chlorobenzyl)sulfonium hexafluoroantimonate in the form of white crystals of melting point 130°–132° C.

$^1$H-NMR (100 MHz, d$_6$-acetone) in ppm: 5.45 (quarter, 4 H); 7.34–8.13 (multiplet, 12 H).

EXAMPLE 12

(a) In a reaction vessel equipped with stirrer and thermometer, 108.23 (0.45 mol) of sodium sulfide hydrate and 6.0 g of tetrabutylammonium hydrogen sulfate are dissolved at RT in 120 ml of water. 105.96 g (0.6 mol) of 1-chloromethylnaphthalene are dissolved in 200 ml of toluene, and this solution is added dropwise to the initially introduced mixture over a period of ½ hour at such a rate that the inside temperature is 40°–50° C. After the dropwise addition, stirring of the reaction mixture at RT is continued for 2½ hours, and the mixture is then filtered. The residue is dissolved in about 500 ml of methylene chloride, and the solution is washed 3 times with water. The organic phase is then dried with MgSO$_4$, and the solvent is removed on a rotary evaporator. 250 ml of isopropanol are then added to the residue formed. This mixture is stirred at RT and then at 0°–5° C. for 1½ hours each time, then filtered, and the residue is dried at RT overnight in a high vacuum. 69.9 g of the dried crude product are dissolved in 785 ml of refluxing isopropanol/acetone (1:1) and then allowed to crystallize at 0°–5° C. for 3 hours. The suspension is filtered, and the residue is washed with a small amount of isopropanol. It is then dried at RT overnight in a high vacuum. This gives 53.2 g (76% of theory) of bis(1-naphthylmethyl) sulfide in the form of white crystals of melting point 104°–106° C.

Elemental analysis Calculated: (%) C=84.03 H=5.77 S=10.2; Found: (%) C=83.85 H=5.8 S=10.25.

$^1$H-NMR (100 MHz, CDCl$_3$) in ppm: 4.13 (singlet, 4 H); 7.25–8.0 (multiplet, 14 H).

(b) 5.0 g (15.9 mmol) of bis(1-naphthylmethyl) sulfide and 5.93 g (17.5 mmol) of triethyloxonium hexafluoroantimonate in 30 ml of methylene chloride are reacted according to Example 1(a) to give 9.07 g (98% of theory) of bis(1-naphthylmethyl)ethylsulfonium hexafluoroantimonate in the form of white crystals of melting point 101°–105° C.

Elemental analysis Calculated: (%) C=49.76 H=4.0 S=5.53 Sb=21.02 F=19.68; Found: (%) C=52.2 H=4.2 S=5.1 Sb=21.3 F=18.1.

$^1$H-NMR (100 MHz, d$_6$-acetone) in ppm: 1.34 (triplet, 3 H); 3.77 (quartet, 2 H); 5.50 (quartet, 4 H); 7.49–8.15 (multiplet, 14 H).

EXAMPLE 13

(a) 13.25 g (42.14 mol) of bis(1-naphthylmethyl) sulfide and 8.0 g (50.6 mmol) of 1-hydroxymethylnaphthalene in 50 ml of methylene chloride are initially introduced at RT under an N$_2$ atmosphere into a reaction vessel equipped with stirrer and thermometer. 17.2 g (105.4 mmol) of HBF$_4$ (54% in diethyl ether) are added dropwise over a period of 25 minutes at such a rate that the inside temperature does not exceed 30° C. The mixture is then stirred at RT and at 30°–35° C. for 2 hours each time. 2 g of 1-hydroxymethylnaphthalene dissolved in 5 ml of methylene chloride are added dropwise to the reaction mixture over a period of 10 minutes, and the reaction is completed at 30°–35° C. for 1½ hours. The reaction mixture is diluted with methylene chloride and washed 4 times with water (pH~7). The organic phase is then dried with MgSO$_4$, and the solvent is removed on a rotary evaporator. The residue is stirred at 0°–5° C. in portions with toluene until crystals can be isolated which are easy to filter. The residue which has been filtered off is dried at RT for about 20 hours in a high vacuum. This gives 21.37 g (93.5% of theory) of tris(1-naphthylmethyl)sulfonium tetrafluoroborate in the form of white-greyish crystals of melting point 115°-120° C. with decomposition.

Elemental analysis Calculated: (%) C=73.01 H=5.02 S=5.91; Found: (%) C=75.9 H=5.4 S=5.25.

(b) A mixture of 15.0 g (27.7 mmol) of tris(1-naphthylmethyl)sulfonium tetrafluoroborate in 100 ml of methylene chloride is initially introduced at RT under an $N_2$ atmosphere into a reaction vessel equipped with stirrer and thermometer, and 10.73 g (41.5 mmol) of sodium hexafluoroantimonate are added. The suspension is stirred for 4 hours, then filtered, and the filtrate is evaporated to dryness. The residue is stirred at 0°-5° C. in 50 ml of methanol/water (1:1) for about 1 hour, the mixture is filtered, and the residue is stirred again at 0°-5° C. in 50 ml of isopropanol for 2 hours. After filtration, the residue is dried at RT overnight in a high vacuum. This gives 10.3 g (53.8% of theory) of tris-(1-naphthylmethyl)sulfonium hexafluoroantimonate in the form of white-grey crystals of decomposition point 120°-125° C.

EXAMPLE 14

(a) In a reaction vessel equipped with stirrer and thermometer, 20.4 g (84.8 mmol) of sodium sulfide hydrate and 1.0 g of tetrabutylammonium hydrogen sulfate are dissolved in 25 ml of water at RT. 25.0 g (113 mmol) of 2-bromomethylnaphthalene are dissolved in 35 ml of toluene and added dropwise over a period of 20 minutes at such a rate that the inside temperature of the reaction mixture is 40°-50° C. After the dropwise addition, the reaction mixture is stirred at RT for 2½ hours. The reaction mixture is diluted with toluene, and the organic phase is washed 3 times with water. The organic phase is dried with $MgSO_4$, and the solvent is removed on a rotary evaporator. The crude product is dissolved in 315 ml of refluxing acetone/isopropanol (1:1), filtered while hot, and the solution is cooled to room temperature. The product is then allowed to crystallize at 0°-5° C. for ½ hour. The mixture is filtered, and the residue is dried at RT overnight in a high vacuum. This gives 13.25 g (74.5% of theory) of bis(2-naphthylmethyl) sulfide in the form of white crystals of melting point 119°-121° C.

Elemental analysis Calculated: (%) C=84.03 H=5.77 S=10.2; Found: (%) C=84.0 H=5.83 S=10.47.

$^1$H-NMR (100 MHz, $d_6$-acetone) in ppm: 3.86 (singlet, 4 H); 7.44-7.92 (multiplet, 14 H).

(b) A mixture of 5.0 mmol) of bis(2-naphthylmethyl) sulfide and 5.93 g (17.49 mmol) of triethyloxoniumhexafluoroantimonate in 40 ml of methylene chloride is stirred at RT under nitrogen for 4 hours. The colourless solution is diluted with methylene chloride and extracted with water (pH~7). The organic phase is then dried with $MgSO_4$ and the methylene chloride is removed on a rotary evaporator. The crude product is stirred in 40 ml of toluene at 0°-5° C. for 1 hour, the residue is filtered and dried at RT overnight in a high vacuum. This gives 8.68 g of bis(2-naphthylmethyl)ethylsulfonium hexafluoroantimonate in the form of white crystals (94.25% of theory) of melting point 152°-153° C.

Elemental analysis Calculated: (%) C=49.77 H=4.0 S=5.53; Found: (%) C=49.85 H=4.1 S=6.34.

$^1$H-NMR (100 MHz, $d_6$-acetone) in ppm: 1.50 (triplet, 3 H); 3.65 (quartet, 2 H); 5.17 (singlet, 4 H); 7.55-8.14 (multiplet, 14 H).

EXAMPLE 15

(a) In a reaction vessel equipped with stirrer and thermometer, 10.72 g (50 mmol) of dibenzyl sulfide are dissolved in 25 ml of methylene chloride at RT, and the solution is cooled to 0°-5° C. 12.19 g of $HBF_4$ (54% in diethyl ether) are added dropwise over a period of 5 minutes under an $N_2$ atmosphere and the introduction of propylene gas is started. The introduction of propylene gas is continued until virtually no more dibenzyl sulfide can be detected in the reaction mixture (detection method: thin layer: silica gel F60; mobile phase: methylene chloride/methanol (95:5)). The reaction mixture is diluted with methylene chloride and washed 3 times with water (pH~7). The organic phase is dried over $MgSO_4$, the solvent is removed on a rotary evaporator, and the residue is stirred in 50 ml of toluene at 0°-5° C. for about 2 hours. Afterwards, the suspension is filtered, and the residue is dried at RT overnight in a high vacuum. This gives 9 g (52.3% of theory) of dibenzylisopropylsulfonium tetrafluoroborate in the form of white crystals of melting point 67°-69° C.

Elemental analysis Calculated: (%) C=59.32 H=6.15 S=9.31; Found: (%) C=59.5 H=6.2 S=9.3.

(b) A mixture of 3.44 g (10 mmol) of dibenzylisopropylsulfonium tetrafluoroborate in 15 ml of methylene chloride is initially introduced into a 3-necked flask under nitrogen at RT and cooled to 0°-5° C. After the addition of 3.88 g (15 mmol) of sodium hexafluoroantimonate, the reaction mixture is stirred at 0°-5° C. for 2-3 hours. The suspension is filtered, and the methylene chloride is removed from the filtrate on a rotary evaporator. The residue is again stirred in 20 ml of water for 1 hour, the mixture is filtered, and the residue is dried at RT overnight in a high vacuum. This gives 4.33 g (88% of theory) of dibenzylisopropylsulfonium hexafluoroantimonate in the form of white crystals of melting point 103°-106° C.

Elemental analysis Calculated: (%) C=41.4 H=4.29 S=6.5; Found: (%) C=41.8 H=4.4 S=6.74.

EXAMPLE 16

(a) In a reaction vessel equipped with stirrer and thermometer, 8.75 g (50 mmol) of α,α,-dichloro-p-xylene and 18.6 g (150 mmol) of benzyl mercaptan are stirred in 60 ml of toluene, until a clear solution is obtained. 200 mg of tetrabutylammonium hydrogen sulfate are partially dissolved in 14 g of 50% aqueous sodium hydroxide solution, and the mixture is added dropwise to the reaction mixture over a period of 10 minutes at such a rate that the inside temperature does not exceed 45° C. 10 ml of toluene and 5 ml of water are added to the reaction mixture, which is then stirred at RT for 2½ hours. The reaction mixture is diluted with toluene, and the organic phase is extracted several times with water (pH~7). It is dried with $MgSO_4$, the solvent is removed on a rotary evaporator, and the residue is allowed to stand for 2 days. The crude product is dissolved in 100 ml of refluxing isopropanol, and the mixture is allowed to cool to RT. The product is then allowed to crystallize at 0°-5° C. for 3 hours. The suspension is filtered and the residue is dried at RT overnight in a high vacuum. This gives 15.32 g (87.4% of theory) of p-xylylenedi(benzyl sulfide) of melting point 64°-66° C.

Elemental analysis Calculated: (%) C=75.38 H=6.33 S=18.29; Found: (%) C=74.9 H=6.55 S=18.35.

$^1$H-NMR (100 MHz in CDCl$_3$) in ppm: 3.59 (multiplet, 8 H); 7.25 (multiplet, 14 H).

(b) A mixture of 1.75 g (5 mmol) of p-xylylenedi(benzyl sulfide) in 20 ml of methylene chloride is stirred in a 3-necked flask under nitrogen at RT, until a solution is obtained. 2.73 g (8.1 mmol) of triethyloxonium hexafluoroantimonate are added to the mixture, which is then stirred for 4 hours. Another 0.5 g (1.43 mmol) of triethyloxonium hexafluoroantimonate is added, and the reaction mixture is stirred overnight. The reaction mixture is cooled to 0°–5° C. and filtered. The residue is stirred in 25 ml of water for 1 hour, the mixture is filtered, and the crude product is dried at RT overnight in a high vacuum. The crude product is suspended in 90 ml of methanol and is heated in the refluxing solvent for 3–5 minutes. The suspension is cooled to RT, the product is allowed to crystallize at 0°–5° C. for 2 hours, the suspension is filtered, and the residue is dried at RT overnight in a high vacuum. This gives 2.53 g (59.9% of theory) of p-xylylenedi(benzylethylsulfonium)-di(hexafluoroantimonate) in the form of white crystals of melting point 157°–158° C.

$^1$H-NMR (100 MHz, d$_6$-acetone) in ppm: 1.45 (triplet, 2 H); 3.55 (quartet, 1 H); 4.94 (singlet, 4 H); 4.98 (singlet, 4 H); 7.5–7.69 (multiplet, 14 H).

EXAMPLE 17

(a) 3.51 g (10 mmol) of p-xylylenedi(benzyl sulfide) according to Example 16(a), 2.7 g (25 mmol) of benzyl alcohol and 4.88 g (30 mmol) of HBF$_4$ (54% in diethyl ether) in 15 ml of methylene chloride and 50 ml of water are reacted analogously to Example 9(b) to give 4.37 g (61.7% of theory) of p-xylylenedi(dibenzylsulfonium) di(tetrafluoroborate) in the form of white crystals of melting point 159°–161° C.

$^1$H-NMR (100 MHz, d$_6$-acetone) in ppm: 4.91 (singlet, 12 H); 7.4 (multiplet, 24 H).

(b) A mixture of 4.0 g (5.65 mmol) of p-xylylenedi(dibenzylsulfonium) di(tetrafluoroborate) is dissolved in 550 ml of acetone in a 3-necked flask with slight warming. At room temperature, 4.38 g (16.94 mmol) of sodium hexafluoroantimonate are added, and the mixture is stirred for 4 hours. After the addition of 600 ml of methylene chloride, the reaction mixture is stirred at 0°–5° C. for 1½ hours and filtered. The solvent is removed from the filtrate on a rotary evaporator, and the residue is stirred in 50 ml of water at RT for 3 hours. The suspension is again filtered, and the residue is dried at RT for 12 hours in a high vacuum. This gives 5.2 g (91% of theory) of p-xylylenedi(dibenzylsulfonium) di(hexafluoroantimonate) in the form of colourless crystals of melting point 130°–133° C.

$^1$H-NMR (100 MHz, d$_6$-acetone) in ppm: 4.95 (singlet, 12 H); 7.40 (multiplet, 24 H).

WORKING EXAMPLES

EXAMPLE A 70 g of bisphenol A diglycidyl ether having an epoxide content of 5.25 equivalents/kg, 30 g of 3',4'-epoxycyclohexylmethyl 3,4-epoxycyclohexanecarboxylate having an epoxide content of 7.1 equivalents/kg and 2 g of dibenzylethylsulfonium hexafluoroantimonate according to Example 1 are homogenized on a triple roll mill to give a fine suspension. The gel time of this mixture is measured at 120° C. on a hot metal plate (gel time plate). The reactivity of the mixture and the glass-transition temperature (T$_G$) are determined in a differential scanning calorimeter (DSC), DSC TA 3000 instrument from Mettler AG, Greifensee, Switzerland, as follows.

1st run (50° to 300° C.; rate of heating 10°/min): measurement of the temperature maximum of the enthalpy peak (peak temperature) and the reaction enthalpy (ΔH).

2nd run (50° to 250° C.; rate of heating 10°/min): measurement of T$_G$ based on the enthalpy jump (average value). The measured results are listed in Table 1.

EXAMPLE B

A mixture is prepared as in Example A, using 2 g of tribenzylsulfonium hexafluoroantimonate according to Example 2 as the sulfonium salt. The gel time, peak temperature, ΔH and T$_G$ are also determined in this mixture. The measured results are shown in Table 1.

EXAMPLE C 1 g of dibenzylethylsulfonium hexafluoroantimonate according to Example 1 is dissolved in 20 g of methylhexahydrophthalic anhydride to give a clear solution. This solution is mixed as in Example A with 70 g of bisphenol A diglycidyl ether and 30 g of 3',4'-epoxycyclohexylmethyl 3,4-epoxycyclohexanecarboxylate having an expoxide content of 7.1 equivalents/kg to give a homogeneous liquid. Gel time, peak temperature, ΔH and T$_G$ are also determined in this formulation. The measured results are shown in Table 1.

EXAMPLE D

A mixture is prepared as in Example C, using 1 g of tribenzylsulfonium hexafluoroantimonate according to Example 2 as the sulfonium salt. Gel time, peak temperature, ΔH and T$_G$ are also determined in this mixture. The measured results are shown in Table 1.

EXAMPLE E

A mixture is prepared as in Example C, using 1 g of tribenzylsulfonium hexafluoroarsenate according to Example 3 as the sulfonium salt. Gel time, peak temperature, ΔH and T$_G$ are also determined in this mixture. The measured results are shown in Table 1.

EXAMPLE F

A homogeneous solution is prepared by heating 100 g of bisphenol A diglycidyl ether according to Example A and 1 g of tribenzylsulfonium hexafluoroantimonate according to Example 2 to about 50° C. Gel time, peak temperature, ΔH and T$_G$ are also determined in this mixture. The measured results are shown in Table 1.

EXAMPLE G

A homogeneous solution is prepared as in Example F by heating 100 f of 3',4'-epoxycyclohexylmethyl 3,4-epoxycyclohexanecarboxylate according to Example A and 1 g of tribenzylsulfonium hexafluoroantimonate according to Example 2 to 50° C. The measured results of this mixture with respect to gel time, peak temperature, ΔH and T$_G$ are shown in Table 1.

EXAMPLES H-1 TO H-14

According to Example C, 1 g of the sulfonium salt of Examples 4 to 17 is in each case dissolved in 20 g of methylhexahydrophthalic anhydride, if necessary with heating to <100° C., and mixed with 70 g of bisphenol A diglycidyl ether and 30 g of 3',4'-epoxycyclohexylmethyl 3,4-epoxycyclohexanecarboxylate to give a homogeneous liquid. The measured results of these mixtures are shown in Table 2.

TABLE 1

Measured results of the mixtures according to Examples A to D

| Mixture according to Example | Gel time at 120°C. [sec] | Peak temperature [°C.] | ΔH [J/g] | Glass-transition temperature $T_G$ [°C.] | Appearance of the resin |
|---|---|---|---|---|---|
| A | 75 | 128 | 567 | 142 | yellowish |
| B | 25 | 115 | 582 | 152 | yellowish |
| C | 140 | 142 | 492 | 154 | light yellow |
| D | 50 | 132 | 520 | 163 | light yellow |
| E | 210 | 132 | 238 | 84 | light yellow |
| F | 75 | 134 | 519 | 170 | light yellow |
| G | 15 | 121 | 595 | —* | light yellow |

*no measurement

TABLE 2

Measured results of Examples H-1 to H-14

| Example | Sulfonium salt according to Example | Gel time at 120° C. [sec] | Peak temperature [°C.] | ΔH [J/g] | $T_G$ [°C.] |
|---|---|---|---|---|---|
| H-1 | 4 | 110 | 128 | 471 | 154 |
| H-2 | 5 | 40 | 127 | 524 | 155 |
| H-3 | 6 | 17 | 113 | 511 | 155 |
| H-4 | 7 | 50 | 131 | 520 | 156 |
| H-5 | 8 | 30 | 128 | 514 | 158 |
| H-6 | 9 | 65 | 130 | 507 | 154 |
| H-7 | 10 | 22 | 122 | 509 | 152 |
| H-8 | 11 | <10 | 94 | 478 | 159 |
| H-9 | 12 | 35 | 124 | 515 | 157 |
| H-10 | 13 | <10 | 106 | 512 | 160 |
| H-11 | 14 | 95 | 137 | 493 | 156 |
| H-12 | 15 | 130 | 138 | 507 | 159 |
| H-13 | 16 | 140 | 142 | 516 | 154 |
| H-14 | 17 | 60 | 124 | 513 | 154 |

EXAMPLES I-1 AND I-2

According to Example C, 1 g of sulfonium salt is dissolved in each case in 20 g of methylhexahydrophthalic anhydride, if necessary with heating to <100° C., and mixed with 50 g of bisphenol A diglycidyl ether and 50 g of bisphenol F diglycidyl ether having an epoxide content of 6.1 equivalents/kg to give a homogeneous liquid. The measured results are shown in Table 3.

TABLE 3

Measured results of Examples I-1 and I-2

| Example | Sulfonium salt according to Example | Gel time at 120° C. [sec] | Peak temperature [°C.] | ΔH [J/g] | $T_G$ [°C.] | Appearance of the resin |
|---|---|---|---|---|---|---|
| I-1 | 2 | 115 | 138 | 518 | 146 | yellow-brown |
| I-2 | 4 | 50 | 130 | 514 | 151 | yellow-brown |

EXAMPLES K-1 TO K-4

1 g of sulfonium salt is dissolved in each case in 10 g of a reactive solvent and mixed with 50 g of bisphenol A diglycidyl ether and 50 g of bisphenol F diglycidyl ether to give a homogeneous liquid. The measured results are shown in Table 4.

TABLE 4

Measured results K-1 to K-4

| Example | Sulfonium salt according to Example | Reactive solvent | Gel time at 120° C. [sec] | Peak temperature [°C.] | ΔH [J/g] | $T_G$ [°C.] |
|---|---|---|---|---|---|---|
| K-1 | 2 | propylene carbonate | 130 | 136 | 541 | 96 |
| K-2 | 2 | ε-Caprolactone | 235 | 138 | 526 | 136 |
| K-3 | 2 | γ-Butyrolactone | 201 | 140 | 528 | 134 |
| K-4 | 4 | Tetrahydrofurfuryl alcohol | 20 | 104 | 515 | 116 |

What is claimed is:

1. A curable mixture containing (a) at least one sulfonium salt of the formula I, II, III or IV

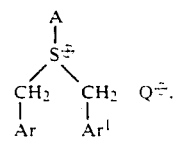

(I)

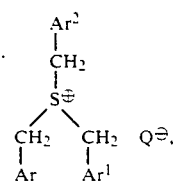

(II)

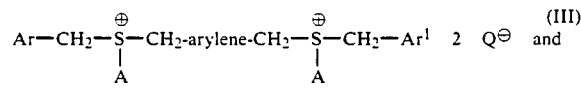

(III)

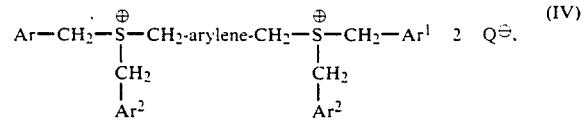

(IV)

in which A is $C_1$-$C_{12}$alkyl, $C_3$-$C_8$cycloalkyl, $C_4$-$C_{10}$cycloalkylalkyl, phenyl which is unsubstituted or mono- or polysubstituted by $C_1$-$C_8$alkyl, $C_1$-$C_4$alkoxy, halogen, nitro, phenyl, phenoxy, alkoxycarbonyl having 1-4 C atoms in the alkoxy radical or acyl having 1-12 C atoms, Ar, $Ar^1$ and $Ar^2$, independently of one another, are each phenyl which is unsubstituted or mono- or polysubstituted by $C_1$-$C_8$alkyl, $C_1$-$C_4$alkoxy, halogen, nitro, phenyl, phenoxy, alkoxycarbonyl having 1-4 C atoms in the alkoxy radical or acyl having 1-12 C atoms or is naphthyl which is unsubstituted or mono-or polysubstituted by $C_1$-$C_8$alkyl, $C_1$-$C_4$alkoxy, halogen, nitro, phenyl, phenoxy, alkoxycarbonyl having 1-4 C atoms in the alkoxy radical or acyl having 1-12 C atoms, each arylene is phenylene which is unsubstituted or mono- or polysubstituted by $C_1$-$C_8$alkyl, $C_1$-$C_4$alkoxy, halogen, nitro, phenyl, phenoxy, alkoxycarbonyl having 1-4 C atoms in the alkoxy radical or acyl having 1-12 C atoms or naphthylene which is unsubstituted or mono-or polysubstituted by $C_1$-$C_8$alkyl, $C_1$-$C_4$alkoxy, halogen, nitro, phenyl, phenoxy, alkoxycarbonyl having 1-4 C atoms in the alkoxy radical or acyl having 1-12 C atoms and $Q^\ominus$ is $SbF_6^-$, $AsF_6^-$ or $SbF_5OH^-$ and (b) at least one cationically polymerizable organic material.

2. A curable mixture according to claim 1, containing a sulfonium salt of the formula I or II.

3. A curable mixture according to claim 1, containing a sulfonium salt of the formula I or II, in which A is $C_1$-$C_{12}$alkyl, Ar, $Ar^1$ and $Ar^2$, independently of one another, are each phenyl which is unsubstituted or mono- or polysubstituted by $C_1$-$C_8$alkyl, $C_1$-$C_4$alkoxy, Cl or Br, and $Q^\ominus$ is $SbF_6^-$ or $SbF_5OH^-$.

4. A curable mixture according to claim 1, containing tribenzylsulfonium hexafluoroantimonate as the sulfonium salt.

5. A curable mixture according to claim 1, containing an epoxy resin as the cationically polymerizable organic material.

6. A curable mixture according to claim 1, additionally containing (c) a heat-curing agent.

7. A curable mixture according to claim 6, containing a polycarboxylic anhydride as the heat-curing agent.

8. A polymerized organic material obtained by heat-curing of a mixture according to claim 1.

* * * * *